US010774376B2

(12) United States Patent
Clemens et al.

(10) Patent No.: US 10,774,376 B2
(45) Date of Patent: *Sep. 15, 2020

(54) QUANTITATING HIGH TITER SAMPLES BY DIGITAL PCR

(71) Applicant: ABBOTT MOLECULAR INC., Des Plaines, IL (US)

(72) Inventors: John M. Clemens, Wadsworth, IL (US); Eric B. Shain, Glencoe, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 385 days.

This patent is subject to a terminal disclaimer.

(21) Appl. No.: 14/980,403

(22) Filed: Dec. 28, 2015

(65) Prior Publication Data

US 2016/0130636 A1 May 12, 2016

Related U.S. Application Data

(63) Continuation of application No. 13/337,784, filed on Dec. 27, 2011, now Pat. No. 9,222,886.

(60) Provisional application No. 61/427,401, filed on Dec. 27, 2010.

(51) Int. Cl.
C12Q 1/686 (2018.01)
C12Q 1/6851 (2018.01)
G01N 21/64 (2006.01)

(52) U.S. Cl.
CPC ........... *C12Q 1/686* (2013.01); *C12Q 1/6851* (2013.01); *G01N 21/6428* (2013.01); *G01N 2021/6441* (2013.01)

(58) Field of Classification Search
None
See application file for complete search history.

(56) References Cited

U.S. PATENT DOCUMENTS

| | | | |
|---|---|---|---|
| 3,710,933 A | 1/1973 | Fulwyler et al. | |
| 4,230,685 A | 10/1980 | Senyei et al. | |
| 4,354,114 A | 10/1982 | Karnaukhov et al. | |
| 4,361,400 A | 11/1982 | Gray et al. | |
| 4,661,225 A | 4/1987 | Penniman et al. | |
| 4,710,472 A | 12/1987 | Saur et al. | |
| 4,812,394 A | 3/1989 | Dolbeare et al. | |
| 4,908,112 A | 3/1990 | Pace | |
| 5,104,791 A | 4/1992 | Abbott et al. | |
| 5,210,015 A | 5/1993 | Gelfand et al. | |
| 5,472,881 A | 12/1995 | Beebe et al. | |
| 5,538,848 A | 7/1996 | Livak et al. | |
| 5,627,054 A | 5/1997 | Gillespie | |
| 5,637,469 A | 6/1997 | Wilding et al. | |
| 5,863,736 A | 1/1999 | Haaland | |
| 5,945,283 A | 8/1999 | Kwok et al. | |
| 6,025,139 A | 2/2000 | Yager et al. | |
| 6,565,727 B1 | 5/2003 | Shenderov | |
| 6,773,566 B2 | 8/2004 | Shenderov | |
| 6,911,132 B2 | 6/2005 | Pamula et al. | |
| 7,198,897 B2 | 4/2007 | Wangh et al. | |
| 7,632,642 B2 | 12/2009 | Wangh et al. | |
| 7,842,248 B2 | 11/2010 | McAvoy et al. | |
| 7,851,184 B2 | 12/2010 | Pollack et al. | |
| 8,349,276 B2 | 1/2013 | Pamula et al. | |
| 9,222,886 B2 * | 12/2015 | Clemens | G01N 21/6428 |
| 10,590,476 B2 * | 3/2020 | Furlan | C12Q 1/686 |
| 2001/0036632 A1 | 11/2001 | Yu et al. | |
| 2004/0053254 A1 | 3/2004 | Wangh et al. | |
| 2004/0175717 A1 | 9/2004 | Van Zyl | |
| 2005/0130176 A1 | 6/2005 | Vogelstein et al. | |
| 2006/0177841 A1 | 8/2006 | Wangh et al. | |
| 2006/0254933 A1 | 11/2006 | Adachi et al. | |
| 2008/0280292 A1 | 11/2008 | Wangh et al. | |
| 2010/0163412 A1 | 7/2010 | Attinger et al. | |
| 2010/0173394 A1 | 7/2010 | Colston, Jr. et al. | |
| 2010/0236929 A1 | 9/2010 | Pollack et al. | |
| 2010/0311599 A1 | 12/2010 | Wheeler et al. | |
| 2013/0302792 A1 * | 11/2013 | Hindson | G01N 21/6486 435/6.1 |

FOREIGN PATENT DOCUMENTS

WO WO-9722719 A1 6/1997
WO WO-9740383 A1 10/1997

OTHER PUBLICATIONS

Shen et al., "Digital PCR on a SlipChip," Lab on a Chip, epublished July, vol. 10, No. 20, pp. 2637-2824. (Year: 2010).*
Zimmerman et al., "Technical Aspects of Quantitative Competitive PCR", BioTechniques, vol. 21, No. 2, pp. 268-279. (Year: 1996).*
Compton J., "Nucleic Acid Sequence-Based Amplification," Nature, 1991, vol. 350 (6313), pp. 91-92.
Final Office Action dated Sep. 12, 2013 for U.S. Appl. No. 13/337,784, filed Dec. 27, 2011.
Gibson U.E., et al., "A Novel Method for Real Time Quantitative RT-PCR," Genome Research, 1996, vol. 6 (10), pp. 995-1001.
Greiner T.C., et al al., "Effectiveness of Capillary Electrophoresis using Fluorescent-Labeled Primers in Detecting T-Cell Receptor Gamma Gene Rearrangements," Journal of Molecular Diagnostics, 2002, vol. 4 (3), pp. 137-143.
Heid C.A., et al., "Real Time Quantitative PCR," Genome Research, 1996, vol. 6 (10), pp. 986-994.
Hindson B.J., et al., "High-Throughput Droplet Digital PCR System for Absolute Quantitation of DNA Copy Number," Analytical Chemistry, 2011, vol. 83 (22), pp. 8604-8610.
Holland P.M., et al., "Detection of Specific Polymerase Chain Reaction Product by Utilizing the 5'----3' Exonuclease Activity of Thermus Aquaticus DNA Polymerase," Proceedings of the National Academy of Sciences, 1991, vol. 88 (16), pp. 7276-7280.

(Continued)

*Primary Examiner* — Young J Kim
(74) *Attorney, Agent, or Firm* — Casimir Jones, S.C.; Kirk Hogan

(57) ABSTRACT

The present invention provides systems, devices, methods, kits, and compositions for nucleic acid analysis using digital PCR. In particular, methods are provided to analyze high titer samples that cannot be divided into a sufficient number of partitions containing zero nucleic acid molecules per partition to allow for Poisson analysis (digital PCR analysis).

11 Claims, 2 Drawing Sheets

(56) References Cited

OTHER PUBLICATIONS

International Search Report and Written Opinion for Application No. PCT/US2011/067366, dated May 2, 2012, 10 pages.
Kiss M.M., et al., "High-throughput Quantitative Polymerase Chain Reaction in Picoliter Droplets," Analytical Chemistry, 2008, vol. 80 (23), pp. 8975-8981.
Kopp M.U., et al., "Chemical Amplification: Continuous-Flow PCR on a Chip," Science, 1998, vol. 280 (5366), pp. 1046-1048.
Livak K.J., et al., "Oligonucleotides with Fluorescent Dyes at Opposite Ends Provide a Quenched Probe System Useful for Detecting PCR Product and Nucleic Acid Hybridization," PCR Methods and Applications, 1995, vol. 4 (6), pp. 357-362.
Lun F.M., et al., "Microfluidics Digital PCR Reveals a Higher than Expected Fraction of Fetal DNA in Maternal Plasma," Clinical Chemistry, 2008, vol. 54 (10), pp. 1664-1672.
Margulies M., et al., "Genome Sequencing in Microfabricated High-Density Picolitre Reactors," Nature, 2005, vol. 437 (7057), pp. 376-380.
Meier V.S., et al., "Simultaneous Evaluation of T- and B-Cell Clonality, t(11;14) and t(14;18), in a Single Reaction by a Four-Color Multiplex Polymerase Chain Reaction Assay and Automated High-Resolution Fragment Analysis: A Method for the Rapid Molecular Diagnosis of Lymphoproliferative Disorders Applicable to Fresh Frozen and Formalin-Fixed, Paraffin-Embedded Tissues, Blood, and Bone Marrow Aspirates," American Journal of Pathology, 2001, vol. 159 (6), pp. 2031-2043.
Nakano M., et al., "Single-Molecule PCR Using Water-in-Oil Emulsion," Journal of Biotechnology, 2003, vol. 102 (2), pp. 117-124.
Neri B.P., et al., "Transferring Automation for Large-scale Development and Production of InvaderTM SNP Assays," In Advances in Nucleic Acid and Protein Analyses, 2000, vol. 3926, pp. 117-125.
Non-Final Office Action dated Feb. 13, 2013 for U.S. Appl. No. 13/337,784 filed Dec. 27, 2011.
Piatek A.S., et al., "Molecular Beacon Sequence Analysis for Detecting Drug Resistance in *Mycobacterium tuberculosis*," Nature Biotechnology, 1998, vol. 16 (4), pp. 359-363.
Ramakrishnan R., "Application of Digital PCR for Basic Research and Clinical Investigation," American Biotechnology Laboratory, 2009, vol. 27 (8), pp. 11-13.
Sanchez J.A., et al., "Linear-After-the-Exponential (LATE)-PCR: An Advanced Method of Asymmetric PCR and its Uses in Quantitative Real-Time Analysis," Proceedings of the National Academy of Sciences, 2004, vol. 101 (7), pp. 1933-1938.
Sohn L.L., et al., "Capacitance Cytometry: Measuring Biological Cells One by One," Proceedings of the National Academy of Sciences, 2000, vol. 97 (20), pp. 10687-10690.
Taira S., et al., "Immobilization of Single-Stranded DNA by Self-Assembled Polymer on Gold Substrate for a DNA Chip," Biotechnology and Bioengineering, 2005, vol. 89 (7), pp. 835-838.
Thelwell N., et al., "Mode of Action and Application of Scorpion Primers to Mutation Detection," Nucleic Acids Research, 2000, vol. 28 (19), pp. 3752-3761.
Tyagi S., et al., "Molecular Beacons: Probes that Fluoresce Upon Hybridization," Nature Biotechnology, 1996, vol. 14 (3), pp. 303-308.
Tyagi S., et al., "Multicolor Molecular Beacons for Allele Discrimination," Nature Biotechnology, 1998, vol. 16 (1), pp. 49-53.
Van Dilla M.A., et al., "Flow Cytometry: Instrumentation and Data Analysis, Book Review" Cytometry, 1986, vol. 7, pp. 495.

\* cited by examiner

QUANTITATING HIGH TITER SAMPLES BY DIGITAL PCR

The present application is a continuation of U.S. application Ser. No. 13/337,784 filed Dec. 27, 2011, which claims priority to U.S. Provisional Application Ser. No. 61/427,401 filed Dec. 27, 2010, the entirety of each of which is incorporated by reference herein.

FIELD OF THE INVENTION

The present invention provides systems, devices, methods, kits, and compositions for nucleic acid analysis using digital PCR. In particular, methods are provided to analyze high titer samples that cannot be divided into a sufficient number of partitions containing zero nucleic acid molecules per partition to allow for Poisson analysis (digital PCR analysis).

BACKGROUND

Digital polymerase chain reaction (dPCR) is a refinement of conventional PCR methods that can be used to directly quantify and clonally amplify nucleic acids. Conventional PCR assumes that amplification is exponential. Therefore, nucleic acids may be quantified by comparing the number of amplification cycles and amount of PCR end-product to those of a reference sample. However, many factors complicate this calculation, creating uncertainties and inaccuracies, including: non-exponential amplification of initial cycles, amplification plateaus, low initial concentrations of target nucleic acid molecules, and differences in amplification efficiency between target and reference sequences. Digital PCR is designed to quantitate target nucleic acid sequences by partitioning the PCR reaction into a sufficient number of reaction subvolumes so that the target is in limiting dilution, i.e., producing a sufficient number of reaction subvolumes with zero target copies so as to allow the application of Poisson statistics. Quantitation is achieved by running the reaction through a fixed number of cycles, sufficient to suitably amplify 1 copy to a detectable response and then counting the number of reactive and non-reactive subvolumes. Quantitation is based on application of Poisson statistics, notably using the number of non-reactive subvolumes to establish the number of initial copies that were distributed across all the reaction subvolumes. However, digital PCR typically requires that a sample be partitioned into many subvolumes such that a significant number of these subvolumes contain zero target nucleic acid molecules. Problems for quantitation by digital PCR arise when the concentration of nucleic acid molecules is too high such that the number of subvolumes containing zero target is nonexistant or is too low to apply Poisson statistics. Conventional dPCR is impractical for applications where the dynamic range is large, e.g., >$10^6$ copies per reaction. In high titer samples, even after dividing a sample into a large number of partitions, it may not be possible to create a population of zero target subvolumes without creating an impractically high number of subvolumes. What are needed are methods to accurately quantitate samples using the digital PCR format in which partitions contain as many as 10, 100, or more target molecules.

SUMMARY OF THE INVENTION

In some embodiments, the present invention provides methods of quantitating a target nucleic acid sequence in a sample comprising: (a) separating the sample into a plurality of partitions, wherein the sample comprises: a mixture of nucleic acid molecules, amplification reagents, detection reagents, and an internal standard sequence that has the same primer binding sequences as the target sequence; wherein a portion of the plurality of partitions contain one or more internal standard molecules and a portion of the plurality of partitions contain zero internal standard molecules; (b) treating the plurality of partitions under amplification conditions such that the target sequences are amplified to produce detectable target amplicons, and the internal standard sequences are amplified to produce detectable internal standard amplicons, wherein the detectable target amplicons and the detectable internal standard amplicons are differentially detectable; (c) determining the change in amplification of the target sequence in response to primer competition from the internal standard sequence; and (d) calculating the initial number of target sequences for the sample. In some embodiments, the plurality of partitions comprises, on average, 2 or more target nucleic acid molecules per partition (e.g., 2-100). In some embodiments, the plurality of partitions comprises, on average, 10 or more target nucleic acid molecules per partition (e.g., 10-100). In some embodiments, the plurality of partitions comprises, on average, 100 or more target nucleic acid molecules per partition. In some embodiments, the amplification reagents comprise primers configured to hybridize to identical sequences in the target sequence and the internal standard sequence. In some embodiments, the detection reagent comprise a first labeled probe configured to bind to the target sequence, and a second labeled probe configured to bind to the internal standard sequence, wherein the first labeled probe and the second labeled probe are differentially detectable. In some embodiments, the first labeled probe and the second labeled probe comprise different fluorescent labels. In some embodiments, the sample is selected from an environmental sample, a biological sample, a clinical sample, and a forensic sample.

In some embodiments, the present invention provides methods of extending the dynamic range of a non-symmetric nucleic acid amplification process comprising: (a) partitioning a sample into a plurality of partitions, wherein a portion of the partitions contain zero target nucleic acid molecules; and (b) amplifying a nucleic acid target sequence by the non-symmetric nucleic acid amplification process to produce target amplicons. In some embodiments, a plurality of partitions comprises, on average, 2-100 or more nucleic acid molecules per partition. In some embodiments, a non-symmetric amplification process is a linear-after-the-exponential PCR (LATE-PCR) amplification process. In some embodiments, methods further comprise (c) detecting the target amplicons in the plurality of partitions using detection reagents. In some embodiments, detection reagents comprise fluorescent labels. In some embodiments, detection reagents comprise fluorescently labeled probes. In some embodiments, detecting is an end-point detection following the completion of the non-symmetric amplification process.

In some embodiments, the present invention provides methods of quantitating a target nucleic acid sequence in a sample comprising: (a) separating the sample into a plurality of partitions, wherein the sample comprises: a mixture of nucleic acid molecules, amplification reagents for non-symmetric nucleic acid amplification, and detection reagents; (b) amplifying the nucleic acid target sequence by the non-symmetric nucleic acid amplification process to produce target amplicons; (c) detecting the target amplicons in the plurality of partitions using the detection reagents; and (d) correlating the intensity produced by the detection reagents following amplification to the initial concentration of the target nucleic acid sequence in the sample. In some embodiments, the plurality of partitions comprises, on average, 2 or more target nucleic acid molecules per partition (e.g., 2-100). In some embodiments, the plurality of partitions comprises, on average, 10 or more target nucleic acid molecules per partition (e.g., 10-100). In some embodiments, the plurality of partitions comprises, on average, 100 or more target nucleic acid molecules per partition.

In some embodiments, the amplification reagents comprise one excess primer and one limiting primer. In some embodiments, the non-symmetric amplification process is a linear-after-the-exponential PCR (LATE-PCR) amplification process. In some embodiments, the detection reagents comprise fluorescent labels. In some embodiments, the detection reagents comprise fluorescently labeled probes. In some embodiments, detecting is an end-point detection following the completion of the non-symmetric amplification process. In some embodiments, the sample is selected from an environmental sample, a biological sample, a clinical sample, and a forensic sample.

In some embodiments, the present invention provides systems or devices for performing the partitioning, amplification, sorting, and/or quantification methods described herein.

In some embodiments, the present invention provides kits comprising reagents for performing the one or more of the partitioning, amplification, sorting, and/or quantification methods described herein.

BRIEF DESCRIPTION OF THE DRAWINGS

The summary and detailed description is better understood when read in conjunction with the accompanying drawings that are included by way of example and not by way of limitation.

DEFINITIONS

Figure 1:
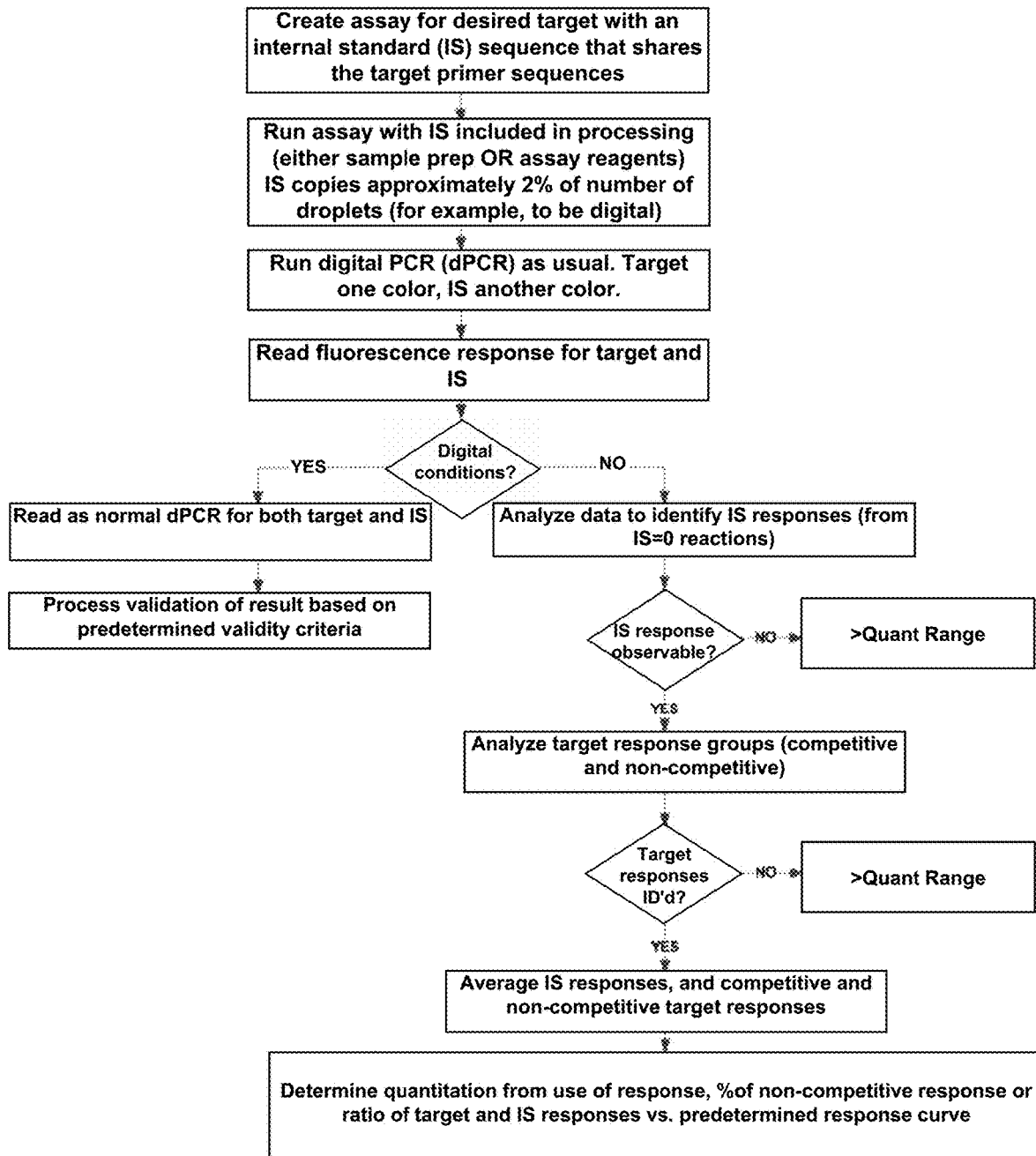
FIG. 1 shows a flow chart providing the design of an embodiment utilizing competitive digital PCR assay.

As used herein, the term "partition" refers to a volume of fluid (e.g. liquid or gas) that is a separated portion of a bulk volume. A bulk volume may be partitioned into any suitable number (e.g. $10^2 \ldots 10^3 \ldots 10^4 \ldots 10^5 \ldots 10^6 \ldots 10^7$, etc.) of smaller volumes (i.e. partitions). Partitions may be separated by a physical barrier or by physical forces (e.g. surface tension, hydrophobic repulsion, etc.). Partitions generated from the larger volume may be substantially uniform in size (monodiperese) or may have non-uniform sizes (polydisperse). Partitions may be produced by any suitable manner (e.g. emulsion, microfluidics, microspray, etc.). Exemplary partitions are droplets. Partitions are referred to as "subvolumes" and "microvolumes."

As used herein, the term "droplet" refers to a small volume of liquid that is immiscible with its surroundings (e.g. gases, liquids, surfaces, etc.). A droplet may reside upon a surface, be encapsulated by a fluid with which it is immiscible (e.g. the continuous phase of an emulsion, a gas (e.g. air, nitrogen)), or a combination thereof. A droplet is typically spherical or substantially spherical in shape, but may be non-spherical. The shape of an otherwise spherical or substantially spherical droplet may be altered by deposition onto a surface or constriction in a capillary channel of smaller diameter. A droplet may be a "simple droplet" or a "compound droplet," wherein one droplet encapsulates one or more additional smaller droplets. The volume of a droplet and/or the average volume of a set of droplets provided herein is typically less than about one microliter (e.g. 0.1 µL . . . 10 nL . . . 1 nL . . . 0.1 nL . . . 10 pL . . . 1 pL . . . 0.1 pL . . . 100 fL . . . 10 fL . . . 1 fL). The diameter of a droplet and/or the average diameter of a set of droplets provided herein is typically less than about one millimeter (e.g. 1 mm . . . 100 µm . . . 10 µm . . . 1 µm). Droplets may be formed by any suitable technique (e.g. emulsification, microfluidics, injection etc.) and may be monodisperse (e.g., substantially monodisperse) or polydisperse.

As used herein, the term "packet" refers to a set of droplets or other isolated partitions disposed in the same continuous volume, in the same region of a continuous volume, on the same surface, or otherwise grouped. A packet may constitute all of the droplets of bulk volume (e.g. an emulsion), or a segregated fraction of droplets from a bulk volume (e.g. at a range of positions along a channel, containing the same target amplicon, etc.). A packet may constitute all the droplets located along a surface (e.g. chip or microfluidic surface), or the droplets in a defined region of a surface. A packet may refer to a set of droplets that when analyzed in partial or total give a statistically relevant sampling for quantitative analysis of the entire starting sample (e.g. the entire bulk volume).

As used herein, the term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. Generation of multiple DNA copies from one or a few copies of a target or template DNA molecule during a polymerase chain reaction (PCR), isothermal reaction, or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, the term "digital PCR" (dPCR) refers to a nucleic acid amplification method for the quantitation and analysis of target nucleic acid sequences by partitioning the reaction into a sufficient number of reaction subvolumes so that the target is in limiting dilution, i.e., producing a sufficient number of reaction subvolumes with zero target copies so as to allow the application of Poisson statistics.

As used herein, "digital PCR methods" refer to the use of one or more of the steps typically employed by dPCR, but does not require that the "digital assumption" be achieved, namely, the assumption that any reaction subvolume that produced target amplicons had a single initial copy of the target sequence.

As used herein, the term "sample" refers to anything capable of being analyzed by the methods provided herein. In some embodiments, the sample comprises or is suspected to comprise one or more nucleic acids capable of analysis by the methods. Preferably, the samples comprise nucleic acids (e.g., DNA, RNA, cDNAs, microRNA, mitochondrial DNA, etc.). Samples may be complex samples or mixed samples, which contain nucleic acids comprising multiple different nucleic acid sequences (e.g. host and pathogen nucleic acids; mutant and wild-type species; heterogeneous tumor. Samples may comprise nucleic acids from more than one source (e.g. difference species, different subspecies, etc.), subject, and/or individual. In some embodiments, the methods provided herein comprise purifying the sample or purifying the nucleic acid(s) from the sample. In some embodiments, the sample contains purified nucleic acid. In some embodiments, a sample is derived from a biological, clinical, environmental, research, forensic, or other source.

DETAILED DESCRIPTION

The present invention provides systems, devices, methods, kits, and compositions for analysis of nucleic acid sequences using digital PCR (dPCR). In particular, provided herein are methods to analyze high titer samples (e.g. high nucleic acid concentration) that cannot be divided into partitions such that the number of partitions containing zero nucleic acid molecules per partition is sufficient to apply Poisson statistical analysis. In other words, the number of target copies in the high titer sample significantly exceeds the number of partitions used in the method.

In some embodiments, a sample is analyzed for the presence and/or abundance of target nucleic acid sequences in a potentially complex sample that may contain many different nucleic acid sequences, each of which may or may not contain the target sequence. In some embodiments, whether or not a target nucleic acid is present ina sample is determined. In some embodiments, the amount of target nucleic acid sequence in a potentially complex sample is quantified. In some embodiments, a sample is analyzed to determine the proportion of nucleic acid molecules containing a target sequence of interest. In some embodiments, a complex sample is analyzed to detect the presence and/or measure the abundance or relative abundance or multiple target sequences. In some embodiments, methods provided herein are used to determine what sequences are present in a mixed sample and/or in what relative proportions.

In some embodiments, a sample containing multiple nucleic acid sequences is analyzed by methods described herein. In some embodiments, a sample is a high titer sample, or a sample containing a high concentration of nucleic acids. In some embodiments, because of the mixture of DNA sequences contained in the sample, direct analysis (e.g. detection, quantification, sequencing, etc.) of the nucleic acids in the sample would not allow resolution of the individual nucleic acid sequences contained therein. In some embodiments, the sample is divided into many partitions (e.g. droplets, etc.) using methods described herein (e.g. emulsion, microspray, microfluidics, etc.). In some embodiments, a sample has a high concentration of nucleic acid molecules and therefore cannot be divided into partitions yielding a sufficient number of partitions with 0 target copies to allow for analysis by Poisson statistics. In some embodiments, a sample is divided into many partitions (e.g. $10^2 \ldots 10^3 \ldots 10^4 \ldots 10^5 \ldots 10^6 \ldots 10^7$, etc.), but because of the high nucleic acid concentration, the sample cannot be divided into partitions yielding a sufficient number of partitions with zero target copies to allow for analysis by Poisson statistics. In some embodiments, a high titer sample is one that cannot be partitioned in such a manner as to yield a sufficient number of partitions with zero target copies to allow for analysis by Poisson statistics.

In some embodiments, the present invention provides amplification (e.g. PCR amplification (e.g. digital PCR (e.g. competitive digital PCR, digital PCR LATE, etc.))) of the partitioned nucleic acids of a sample. In some embodiments, amplification reagents (e.g. primers) are added to a sample prior to partitioning and/or concurrent with partitioning, or amplification reagents are added to the partitioned sample, or amplification reagents are partitioned and then joined or coalesced with the partitioned sample. In some embodiments, primers are hybridized to template nucleic acids (e.g. target nucleic acids, internal standards) prior to partitioning or after partitioning.

In some embodiments, detection reagents (e.g., fluorescent labels) are included with amplification reagents added to the bulk or partitioned sample. In some embodiments, amplification reagents also serve as detection reagents. In some embodiments, detection reagents are added to partitions following amplification. In some embodiments, detection reagents comprise fluorescent labels. In some embodiments, amplified target nucleic acids (amplicons) are detectable via detection reagents in their partition. In some embodiments, unamplified and/or non-target nucleic acid molecules are not detected. In some embodiments, partitions are detectable using one or more detection reagents (e.g. fluorescent labels). In some embodiments, the final concentration of amplicons (e.g. target amplicons, internal standard amplicons, etc.) in a partition is quantified using detection reagents (e.g. labels (e.g. fluorescent labels)). In some embodiments, the signal produced by detection reagents (e.g., fluorescence intensity) correlates with amplicon concentration. In some embodiments, measurements of the relative proportion of target nucleic acids in a sample (e.g. relative to other targets nucleic acids, relative to non-target nucleic acids, relative to total nucleic acids, etc.) or the concentration of target nucleic acids in a sample can be measured based on the quantification of amplicons (e.g. target amplicons, internal standard amplicons, etc.) in a plurality partitions. In some embodiments, final target concentration is compared to final internal standard concentration. In some embodiments, the signal from the target amplicon detection reagents is compared to the signal from internal standard (IS) amplicon detection reagents (e.g. to determine final target concentration).

In some embodiments, following amplification, partitions containing amplified target nucleic acids (amplicons) are sorted from partitions not containing amplicons, from partitions not containing nucleic acids, or from amplicons containing other amplified targets. In some embodiment, partitions containing internal standard amplicons are isolated and/or sorted from partitions without internal standard amplicons. In some embodiments, partitions are sorted based on physical, chemical, and/or optical characteristics of the partition, the nucleic acids therein (e.g. concentration), and/or labels therein (e.g. fluorescent labels). In some embodiments, individual partitions are isolated for subsequent manipulation, processing, and/or analysis of the amplicons therein. In some embodiments, partitions containing similar characteristics (e.g. same fluorescent labels, similar nucleic acid concentrations, presence or absence of IS amplicon, etc.) are grouped (e.g. into packets) for subsequent manipulation, processing, and/or analysis (e.g. of the partitions or of the amplicons therein, etc.).

In some embodiments, the present invention provides competitive dPCR (cdPCR). In some embodiments, the present invention overcomes the challenges presented by high titer samples (i.e. high concentration of nucleic acid) through the use of cdPCR. In some embodiments, cdPCR is configured in a competitive amplification format, using an internal standard nucleic acid that shares primer sequences with the target sequence (or target sequences) to be analyzed (e.g. quantitated). In some embodiments, the IS is added such that there are a sufficient number of reaction subvolumes with zero target copies so as to allow the application of Poisson statistics. In some embodiments, the IS is added to the sample at a low enough concentration that, when partitioned, zero or 1 IS copies are present in each partition, prior to amplification. In some embodiments, the amplification of a single copy of the IS competes with amplification of the target sequences in the partitions containing an IS nucleic acid molecule. In some embodiments, the digital assumption cannot be achieved for a target sequence, but can be achieved for the IS. In some embodiments, the present invention provides dPCR reaction conditions for the IS (e.g., partitioned); wherein a significant number of reactions (partitions) have no IS; such that the quantitative interpretation of the IS response is determinable by Poisson analysis. In some embodiments, the exact number of IS copies in a reaction (i.e., partition) is known because the IS is run at a level where only zero or 1 copy is present in any partition. In some embodiments, if a partition contains one initial copy of the IS, the amplification reaction in that partition will produce IS amplicons. In some embodiments, if a partition contains zero initial copies of the IS, the amplification reaction in that partition will not produce IS amplicons. In some embodiments, the calibration required by conventional competitive PCR is not required for cdPCR. In some embodiments, cdPCR allows determination of the percent signal reduction due to competition with IS. In some embodiments, the signal reduction due to competition with IS provides a means for quantitation using cdPCR. In some embodiments, methods of the present invention (e.g. cdPCR) provide analysis of amplification competition between one or more target nucleic acid molecules and one copy of IS. In some embodiments, methods of the present invention provide analysis of amplification competition between one or more target nucleic acid molecules and one or more copies of IS. In some embodiments, the digital assumption is not met for a partitioned sample. In some embodiments, the IS is added to the sample at a concentration that, when partitioned, that does not meet the digital assumption, in that some partitions have more than 1 copy prior to amplification. In some embodiments, the total concentration of IS across all partitions is determined by Poisson analysis. In some embodiments, the IS is carried in the digital assumption. In some embodiments, the IS is not carried in the digital assumption, but is still digitally quantifiable (e.g., via Poisson analysis). In some embodiments, cdPCR provides methods for quantitation of target nucleic acids at the high end of the dynamic range. In some embodiments, cdPCR provide quantification of nucleic acids in a sample in which conventional dPCR is incapable due to the inability to adequately partition the sample into partitions wherein a some portion of the partitions have no target. In some embodiments, multiple IS sequences are provided in a reaction to compete with multiple different target nucleic acid sequences.

In some embodiments, the present invention provides dPCR LATE (linear-after-the-exponential). In some embodiments, the present invention overcomes the challenges presented by high titer (i.e. high concentration of nucleic acid) through the use of dPCR LATE. In some embodiments, dPCR LATE provides the PCR methods known as LATE PCR, or elements thereof (See, e.g. U.S. Pat. App. No. 20060177841; U.S. Pat. No. 7,632,642; herein incorporated by reference in their entireties), in a digital or partitioned format. In some embodiments, dPCR LATE provides linear amplification after the exponential phase. In some embodiments, in dPCR LATE, PCR response curves do not grow exponentially and then plateau, but rather continue to grow in a linear fashion after crossing what would be considered the traditional real-time PCR threshold region of the growth curve. In some embodiments, continued linear growth allows for correlation of the signal intensity at the final cycle with the concentration of the initial target. In some embodiments dPCR LATE provides methods for quantification of the initial target nucleic acid concentration in a partition based on the final amplicon concentration after multiple rounds of dPCR LATE amplification. In some embodiments, quantification of multiple partitions (e.g. 5 . . . 10 . . . 100 . . . 1000 . . . 10,000, etc.) provides quantification of the original bulk sample.

In some embodiments, the methods provided herein (e.g. cdPCR, dPCR LATE, etc.) extend quantitation beyond the range attainable by typical dPCR methods employing Poisson analysis. In some embodiments, methods herein (e.g. cdPCR, dPCR LATE, etc.) extend quantitation of target nucleic acids to sample nucleic acid concentrations where digital assumption (i.e. zero or 1 nucleic acid molecules per partition) and/or reactive/non-reactive ratio methods fail. In some embodiments, methods herein (e.g. cdPCR, dPCR LATE, etc.) are performed in a single reaction (e.g. many partitions within a single reaction volume). In some embodiments, dilution is not required with methods described herein (e.g. cdPCR, dPCR LATE, etc.). In some embodiments, a priori knowledge of the nucleic acid concentration range is not required with methods described herein (e.g. cdPCR, dPCR LATE, etc.). In some embodiments, methods (e.g. cdPCR) provide target nucleic acid quantitation without an assay calibration curve.

In some embodiments, the present invention provides conditions wherein the number of partitions with zero target copies is insufficient to allow the application of Poisson statistics which provides increased quantitation range, increased precision, and/or improved accuracy when measuring the magnitude of small signal responses.

In some embodiments, the present invention provides methods comprising, but not limited to, one or more of the steps of: (I) partitioning of a sample (e.g., droplet generation), (II) amplification. (III) amplicon detection/quantification, and (IV) amplicon sorting/isolation, each of which are addressed below.

I. Partitioning

In some embodiments, the present invention provides systems, devices, and methods for dividing volumes of fluid and/or reagents into partitions (e.g. droplets, microvolumes, subvolumes, etc.). In some embodiments, the present invention utilizes partitioning systems, devices, and/or methods. In some embodiments, exemplary partitioning methods and systems include one or more of emulsification, droplet actuation, microfluidics platforms, continuous-flow microfluidics, reagent immobilization, and combinations thereof.

In some embodiments, partitioning is performed to generate microvolume partitions containing a small number of nucleic acid molecules (e.g. 0-1000, 2-500, 10-100, etc.) compared to the number of nucleic acid molecules present in the bulk sample. In some embodiments, partitioning methods described herein are incapable of achieving 0 or 1 nucleic acid molecules per partition, without undue difficulty (e.g. too many partitions), due to the high concentration of nucleic acid in the bulk sample. In some embodiments, one or more internal standard (IS) nucleic acid molecules are added to a sample before or after partitioning. In some embodiments, the IS is added in sufficiently small enough concentration that each partition contains zero or 1 IS molecules. In some embodiments, the IS is added at a concentration where some partitions may have more than 1 IS molecule. In some embodiments, the IS concentration is determinable using Poisson analysis.

In some embodiments, the present invention provides systems, methods, and devices for partitioning a bulk volume into partitions (e.g. droplets) by emulsification (Nakano et al. J Biotechnol 2003; 102:117-124; Margulies et al. Nature 2005; 437:376-380; herein incorporated by reference in their entireties). In some embodiments, the present invention provides systems and methods for generating "water-in-oil" droplets (U.S. Pat. App. No. 20100173394; herein incorporated by reference in its entirety).

In some embodiments, the present invention provides microfluidics systems, methods, and devices for partitioning a bulk volume into partitions (U.S. Pat. App. No. 20100236929; U.S. Pat. App. No. 20100311599; U.S. Pat. App. No. 20100163412; U.S. Pat. No. 7,851,184; herein incorporated by reference in their entireties). In some embodiments, microfluidic systems are configured to generate monodisperse droplets (Kiss et al. Anal Chem. 2008 Dec. 1; 80(23): 8975-8981; herein incorporated by reference in its entirety). In some embodiments, the present invention provides microfluidics systems for manipulating and/or partitioning samples. In some embodiments, a microfluidics system comprises one or more of channels, valves, pumps, etc. (U.S. Pat. No. 7,842,248, herein incorporated by reference in its entirety). In some embodiments, a microfluidics system is a continuous-flow microfluidics system (Kopp et al., Science, vol. 280, pp. 1046-1048, 1998; herein incorporated by reference in its entirety). In some embodiments, microarchitecture of the present invention includes, but is not limited to microchannels, microfluidic plates, fixed microchannels, networks of microchannels, internal pumps; external pumps, valves, centrifugal force elements, etc. In some embodiments, the microarchitecture of the present invention (e.g. droplet microactuator, microfluidics platform, and/or continuous-flow microfluidics) is complemented or supplemented with droplet manipulation techniques, including, but not limited to electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). In some embodiments, a droplet microactuator is supplemented with a microfluidics platform (e.g. continuous flow components) and such combination approaches involving discrete droplet operations and microfluidics elements are within the scope of the invention.

In some embodiments, the present invention provides a droplet microactuator. In some embodiments, a droplet microactuator is capable of effecting droplet manipulation and/or operations, such as dispensing, splitting, transporting, merging, mixing, agitating, and the like. In some embodiments the invention employs droplet operation structures and techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; U.S. Patent Publication No. 20060254933, entitled "Device for transporting liquid and system for analyzing" published on Nov. 16, 2006 by Adachi et al., the disclosures of which are incorporated herein by reference in their entireties. Droplet manipulation is, in some embodiments, accomplished using electric field mediated actuation. In such embodiments, electrodes are electronically coupled to a means for controlling electrical connections to the droplet microactuator. An exemplary droplet microactuator includes a substrate including a path and/or array of electrodes. In some embodiments, a droplet microactuator includes two parallel substrates separated by a gap and an array of electrodes on one or both substrates. One or both of the substrates may be a plate.

In some embodiments, nucleic acid targets, primers, and/or probes for use in embodiments of the present invention are immobilized to a surface, for example, a substrate, plate, array, bead, particle, etc. In some embodiments, immobilization of one or more reagents provides (or assists in) one or more of: partitioning of reagents (e.g. IS, target nucleic acids, primers, probes, etc.), controlling the number of reagents per partition, and/or controlling the ratio of one reagent to another in each partition. In some embodiments, assay reagents and/or target nucleic acids are immobilized to a surface while retaining the capability to interact and/or react in with other reagents (e.g. reagent dispensed from a microfluidic platform, a droplet microactuator, etc.). In some embodiments, reagents (e.g. IS, target nucleic acids, primers, probes, etc.) are immobilized on a substrate and droplets or partitioned reagents are brought into contact with the immobilized regents. In some embodiments, reagent immobilization is involved in other methods and steps of the present invention (e.g. sequence analysis). Techniques for immobilization of nucleic acids and other reagents to surfaces are well understood by those in the art (See, e.g., U.S. Pat. No. 5,472,881; Taira et al. Biotechnol Bioeng. 2005 Mar. 30; 89(7):835-8); herein incorporated by reference in their entireties).

II. Amplification

In some embodiments, the present invention provides compositions and methods for the amplification of nucleic acids (e.g. DNA, RNA, etc.). In some embodiments, amplification is performed on a sample that has been divided into partitions (e.g. droplets). In some embodiments, an amplification reaction is carried out within each partition. In some embodiments, a partition contains all the reagents necessary for nucleic acid amplification (e.g. primers, polymerase, deoxynucleotides, template (e.g. target, internal standard, etc.), etc.). In some embodiments, amplification is performed using dPCR methods, where the number of subvolumes containing 0 target is nonexistent or is too low to apply Poisson statistics.

In some embodiments, the present invention provides compositions (e.g. primers, buffers, salts, nucleic acid targets, etc.) and methods for the amplification of nucleic acid (e.g. digital PCR, digital droplet amplification, PCR amplification, partitioned amplification, cdPCR, dPCR LATE, combinations thereof, etc.). In some embodiments, an amplification reaction is any reaction in which nucleic acid replication occurs repeatedly over time to form multiple copies of at least one segment of a template or target nucleic acid molecule (e.g. DNA, RNA). In some embodiments, amplification reaction is achieved by repeated thermal cycling. In some embodiments, amplification reaction is achieved isothermally. In some embodiments, amplification generates an exponential or linear increase in the number of copies of the template nucleic acid. Amplifications may produce in excess of a 1,000-fold increase in template copy-number and/or target-detection signal. Exemplary amplification reactions include, but are not limited to the polymerase chain reaction (PCR) or ligase chain reaction (LCR), each of which is driven by thermal cycling. Amplifications used in method or assays of the present invention may be performed in bulk and/or partitioned volumes (e.g. droplets). Alternative amplification reactions, which may be performed isothermally, also find use herein, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like.

Amplification may be performed with any suitable reagents (e.g. template nucleic acid (e.g. DNA or RNA), primers, probes, buffers, replication catalyzing enzyme (e.g. DNA polymerase, RNA polymerase), nucleotides, salts (e.g. $MgCl_2$), etc. In some embodiments, an amplification mixture includes any combination of at least one primer or primer pair, at least one probe, at least one replication enzyme (e.g., at least one polymerase, such as at least one DNA and/or RNA polymerase), and deoxynucleotide (and/or nucleotide) triphosphates (dNTPs and/or NTPs), etc.

In some embodiments, the present invention utilizes nucleic acid amplification that relies on alternating cycles of heating and cooling (i.e., thermal cycling) to achieve successive rounds of replication (e.g., PCR). In some embodiments, PCR is used to amplify target nucleic acids (e.g. partitioned targets). PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. Typical PCR methods produce an exponential increase in the amount of a product amplicon over successive cycles, although linear PCR methods also find use in the present invention.

Any suitable PCR methodology, combination of PCR methodologies, or combination of amplification techniques may be utilized in the partitioned methods (e.g. droplet-based detection, separation, and/or sequencing of target nucleic acids) disclosed herein, such as cdPCR, dPCR LATE, allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, or universal fast walking PCR, etc.

In some embodiments, the present invention provides dPCR methods (See, e.g., Ramakrishnan, American Biotechnology Laboratory 27(8), 11-13 (2009); herein incorporated by reference in its entirety). In some embodiments, PCR is performed on portions of a sample (e.g. partitions) to determine the presence or absence, concentration, and/or copy number of a nucleic acid target in the sample, based on how many of the sample portions support amplification of the target. In some embodiments, PCR is performed on portions of a sample (e.g. partitions) to determine the presence or absence, concentration, and/or copy number of a nucleic acid target in the sample, based on quantitation of subvolume nucleic acid concentration determined by methods described herein (e.g., cdPCR, dPCR LATE). In some embodiments, PCR is performed on portions of a sample (e.g. partitions) to detect more than one target nucleic acid and/or to determine the concentration, and/or relative concentrations of multiple target nucleic acids within a sample. In some embodiments, digital PCR is performed as endpoint PCR (e.g., for each of the partitions). In some embodiments, digital PCR is performed as rtPCR (e.g., for each of the partitions). In some embodiments, digital PCR is performed as dPCR LATE (e.g., for each of the partitions). In some embodiments, digital PCR is performed as cdPCR (e.g., for each of the partitions).

Conventional PCR theoretically results in an exponential amplification of a nucleic acid sequence (e.g. template or target nucleic acid) from a sample over a series of cycles in the early portion of the amplification process. By measuring the number of amplification cycles required to achieve a threshold level of amplification (as in real-time PCR), the starting concentration of nucleic acid can be calculated. However, there are many factors that affect the exponential amplification of the PCR process, such as varying amplification efficiencies, competition of low copy number targets with higher concentration targets for reagents, and interference with background contaminant nucleic acid. Digital PCR is generally less sensitive to these factors, since it does not rely on the assumption that the PCR process is exponential. In digital PCR, individual nucleic acid molecules from the initial sample are distributed amongst the partitions, and then amplified to detectable levels. The distribution of these target nucleic acid molecules across the partitions is governed by Poisson statistics. Quantitation in dPCR is possible whenever there is a sufficient number of 0 target containing partitions to apply Poisson statistics. As the number of 0 target containing partitions decreases approaching zero, the uncertainty in the quantitation value increases, ultimately becoming undefined (infinity) when there are no 0 target containing partitions. In embodiments in which multiple target nucleic acids are analyzed, digital PCR provides statistically relevant measure of the concentrations or ratios to multiple target nucleic acids. In some embodiments, the present invention provides dPCR methods, or elements thereof.

In some embodiments, the present invention provides LATE PCR (U.S. Pat. No. 7,632,642; herein incorporated by reference in its entirety), or elements thereof. In some embodiments LATE PCR methods are performed in a digital format (e.g. dPCR LATE). In some embodiments, LATE PCR methods are performed on a partitioned sample. In some embodiments, LATE PCR techniques are utilized for amplification of a partitioned sample (e.g. digital or non-digital sample). In some embodiments, LATE-PCR or dPCR LATE is a non-symmetric DNA amplification employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce fluorescently detectable double-stranded amplicon, wherein the concentration-adjusted melting temperature of the Limiting Primer at the start of amplification, $T_m[0]^L$, is not more than 5° C. below the concentration-adjusted melting temperature of the Excess Primer at the start of amplification, $T_m[0]^X$, preferably at least as high and more preferably 3-10° C. higher; and wherein thermal cycling is continued for multiple cycles after exhaustion of the Limiting Primer to produce single-stranded product, namely, the extension product of the Excess Primer, sometimes referred to as the "Excess Primer Strand".

In some embodiments, the present invention provides competitive PCR (e.g. cdPCR), or elements thereof. Conventional competitive PCR is a method for target quantitation using end point PCR, which employs the co-amplification of an unknown and IS target sequences that share primer sequences. Since both amplifications consume the same primers, they compete for the available resources. If each reaction has the same efficiency, the relationship of the initial (pre-amplification) concentration of unknown ($T_0$) and IS ($IS_0$) to the final post amplification concentration after j cycles ($T_j$ and $IS_j$) is described by the expression:

$$\mathrm{Log}(T_j/IS_j) = \log(T_0) - \log(IS_0)$$

In conventional competitive PCR applications, utilization of this method requires a priori knowledge of $IS_0$ or a calibration curve to establish the relationship between measured response and unknown concentration. The calibration curve is expressed as:

log(target response/internal standard response) vs. log([target]).

This response produces a relatively straight line curve that allows for subsequent reactions to be quantitated. The curve deviates from linearity based on how similar the amplification efficiencies are for the 2 competitive targets. In general, this method can produce up to approximately 5 logs of quantitation depending on the precision of the response measurements. The problems for quantitation associated with the conventional competitive PCR method include limited dynamic range and imprecision at the extremes of the quantitative range. In addition, this method requires generation of the calibration curve described above due to variation in IS concentration from lot to lot, reaction to reaction, and other factors. In some embodiments, these challenges are overcome by performing competitive PCR in a digital format.

In some embodiments, the present invention utilizes real-time PCR, or elements thereof. In some embodiments, real-time PCR achieves quantitation by reading the fluorescence response of the target PCR reaction at frequent cycle intervals (e.g. every cycle), and identifying the cycle number at which the signal crosses a threshold response value. Quantitation is based on the efficiency of amplification and the number of cycles or amplification events required to produce a detectable concentration of product. The problems for quantitation associated with real-time PCR largely relate to determination of low copy targets in the presence of other amplifications, such as for other high titer targets or non-specific amplifications, e.g., primer dimers. Other challenges include amplification in the presence of non-amplifying nucleic acid (e.g. genomic DNA) that can interfere with the amplification process and suppress low copy amplification responses. Real-time PCR also requires some type of calibration, typically either a calibration curve run within the batch or stored, or a reference quantitation standard (QS) of known concentration run in every reaction that defines the relationship between cycle number and concentration.

In some embodiments, the present invention provides amplification techniques (e.g. dPCR LATE, cdPCR, combinations thereof, etc.) capable of extending the dynamic range for dPCR and achieving precise quantitation at and beyond the upper end of the quantitative range. In some embodiments, amplification and analysis methods described herein (e.g. dPCR LATE, cdPCR, combinations thereof, etc.) provide an extension of the dPCR dynamic range to as much as much as 8 orders of magnitude (e.g. 5 orders of magnitude . . . 6 orders of magnitude . . . 7 orders of magnitude . . . 8 orders of magnitude). In some embodiments, amplification and analysis methods described herein (e.g. dPCR LATE, cdPCR, combinations thereof, etc.) provide an extension of the dPCR dynamic range by up to three logs over what is obtainable by Poisson analysis (e.g., extension of 1 order of magnitude, extension of 2 orders of magnitude, extension of 3 orders of magnitude).

III. Amplicon Detection/Quantification

In some embodiments, a sample is partitioned using any suitable method, and a nucleic acid amplification procedure (e.g. cdPCR, dPCR LATE, etc.) is performed to amplify target nucleic acids present in one or more of the partitions. In some embodiments, a quantification method is provided to quantify the amplicons produced by the amplification reactions in each partition. In some embodiments, quantification is performed following amplification (e.g., end-point detection). In some embodiments quantification is performed in real time (e.g. amplicon quantification following each round of amplification). In some embodiments, the present invention provides systems, devices, methods, and compositions to detect the presence of and/or quantify nucleic acids (e.g. amplicons (e.g. IS amplicons, target amplicons), labeled nucleic acids) in a sample or partition. In some embodiments, the present invention provides detection of the presence of amplicons in partitions. In some embodiments, the present invention provides quantification of amplicons (e.g. IS amplicons, target amplicons) in a partition. In some embodiments, the present invention provides relative quantification of target and IS amplicons. In some embodiments, amplicon quantification involves measurement or detection of a characteristic of partitions and/or amplicons, such as a physical, chemical, luminescence, or electrical aspect, which correlates with amplification (e.g. fluorescence, luminescence, radioactivity, or other detectable signal) and allows amplicon quantification. In some embodiments, amplicon quantification is performed by a fluorescence detection technique.

In some embodiments, fluorescence detection methods are provided for detection/quantification of amplified nucleic acids. In addition to the reagents already discussed, and those known to those of skill in the art of nucleic acid amplification and quantification, various detection reagents, such as fluorescent and non-fluorescent dyes and probes are provided. For example, the protocols may employ reagents suitable for use in a TaqMan™ reaction, such as a TaqMan™ probe; reagents suitable for use in a SYBR Green fluorescence detection; reagents suitable for use in a molecular beacon reaction, such as molecular beacon probes; reagents suitable for use in a scorpion reaction, such as a scorpion probe; reagents suitable for use in a fluorescent DNA-binding dye-type reaction, such as a fluorescent probe; and/or reagents for use in a LightUp protocol, such as a LightUp probe. In some embodiments, the present invention provides methods and compositions for quantifying a detectable signal (e.g. fluorescence) from partitions containing amplified nucleic acid (e.g. target amplicons, IS amplicons, etc.). Thus, for example, methods may employ labeling (e.g. during amplification, post-amplification) amplified nucleic acids with a detectable label, exposing partitions to a light source at a wavelength selected to cause the amplicon bound probe dye to fluoresce, and detecting and/or measuring the resulting fluorescence. Fluorescence emitted from the partitions can be tracked during amplification reaction to permit monitoring of the reaction (e.g., using a SYBR Green-type compound), or fluorescence can be measured post-amplification.

In some embodiments, the present invention provides methods of detecting and/or quantifying the presence of a target nucleic acid in partitions by providing a probe with specificity for a target nucleic acid (e.g., a TaqMan™-type probe) in partitioned amplification reactions, and detecting/measuring the resulting fluorescence. In some embodiments, partitions containing amplified nucleic acid (e.g. target amplicons, IS amplicons, etc.) will exhibit quantifiable post-amplification fluorescence. In some embodiments, detection of a fluorescent signal is indicative of the presence of the template nucleic acid (e.g. IS, target) in the partition.

The present invention provides corresponding methods for using other suitable target-specific probes (e.g. intercalation dyes, scorpion probes, molecular beacons, etc.), as would be understood by one of skill in the art. In some embodiments, the present invention provides quantification of amplified nucleic acids using one or more of fluorescent labeling, fluorescent intercalation dyes, FRET-based detection methods (U.S. Pat. No. 5,945,283; PCT Publication WO 97/22719; both of which are incorporated by reference in their entireties), quantitative PCR, real-time fluorogenic methods (U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety), molecular beacons (Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998); herein incorporated by reference in their entireties), Invader™ assays (Third Wave Technologies, (Madison, Wis.)) (Neri, B. P., et al., Advances in Nucleic Acid and Protein Analysis 3826:117-125, 2000; herein incorporated by reference in its entirety), nucleic acid sequence-based amplification (NASBA; (See, e.g., Compton, J. Nucleic Acid Sequence-based Amplification, Nature 350: 91-91, 1991; herein incorporated by reference in its entirety), Scorpion probes (Thelwell, et al. Nucleic Acids Research, 28:3752-3761, 2000; herein incorporated by reference in its entirety), capacitive DNA detection (See, e.g., Sohn, et al. (2000) Proc. Natl. Acad. Sci. U.S.A. 97:10687-10690; herein incorporated by reference in its entirety), etc.

In some embodiments, labeling methods are used to differentially label different amplicons. In some embodiments, IS amplicons and target amplicons are differentially labeled to allow for separate detection and quantification. In some embodiments, IS amplicons and target amplicons are differentially labeled to allow for sorting of IS-containing partitions from partitions without IS amplicons. In some embodiments, different target sequences are differentially labeled to allow for separate detection and quantification. In some embodiments, different target sequences are differentially labeled to allow for sorting of one target from another. In some embodiments, differential labeling is achieved via sequence specific labeling probes with detectably different fluorescent labels.

IV. Amplicon Isolation

In some embodiments, the present invention provides methods for sorting and/or isolation of amplified nucleic acid. In some embodiments, the present invention provides methods to sort and/or isolate partitions containing amplified nucleic acid. In some embodiments, following amplification of target sequences and/or detection of amplicons, partitions are sorted according to the amplicons contained therein (e.g. IS v. no IS, presence of a particular amplicon, etc.), for subsequent manipulation (e.g. re-amplification, labeling, restriction digestion, etc.) and/or analysis (e.g. sequencing, mass detection, etc.).

In some embodiments, amplicons are labeled with detectable and/or manipulatable labels (e.g. fluorescent dyes), during or after amplification, by accepted methods understood to those in the art (e.g., intercalation, incorporation, hybridization, etc.) In some embodiments, partitions containing labeled amplicons are detected and/or sorted (e.g. segregated from non-amplicon-containing partitions, grouped according to presence of a particular label, etc.). In some embodiments, partitions containing IS amplicons are sorted from partition not containing IS amplicons. For example, in some embodiments, amplicon-containing partitions are mechanically separated by micro-manipulators, electrophoresis, flow cytometry, or other sorting techniques known to those in the art. The following references provide guidance for selecting means for analyzing and/or sorting microparticles: Pace, U.S. Pat. No. 4,908,112; Saur et al., U.S. Pat. No. 4,710,472; Senyei et al., U.S. Pat. No. 4,230,685; Wilding et al., U.S. Pat. No. 5,637,469; Penniman et al., U.S. Pat. No. 4,661,225; Kamaukhov et al., U.S. Pat. No. 4,354,114; Abbott et al., U.S. Pat. No. 5,104,791; Gavin et al., PCT publication WO 97/40383; herein incorporated by reference in their entireties.

In some embodiments, partitions containing fluorescently labeled DNA strands are detected, classified, isolated, and/or sorted by fluorescence-activated cell sorting (FACS; See, e.g., Van Dilla et al., Flow Cytometry: Instrumentation and Data Analysis (Academic Press, New York, 1985); Fulwyler et al., U.S. Pat. No. 3,710,933; Gray et al., U.S. Pat. No. 4,361,400; Dolbeare et al., U.S. Pat. No. 4,812,394; herein incorporated by reference in their entireties. In some embodiments, amplicons are fluorescently labeled with detectable and/or manipulatable fluorescent labels, during or after amplification, by accepted methods understood to those in the art (e.g., intercalation, incorporation, hybridization, etc.). In some embodiments, upon excitation with one or more high intensity light sources, such as a laser, a mercury arc lamp, or the like, each partition containing amplified (and labeled) nucleic acids (e.g. target amplicon, IS amplicon, etc.) will generate fluorescent signals. In some embodiments, partitions exhibiting fluorescence above background, or above a threshold level, are sorted by a FACS instrument, according to methods understood by those of skill in the art. Thus, in some embodiments, partitions are sorted according to their relative optical signal, and collected for further analysis by accumulating those partitions generating a signal within a predetermined range of values corresponding to the presence of amplified target nucleic acid. In some embodiments, partitions are sorted and transferred to reaction vessels and/or platforms suitable for subsequent manipulation, processing, and/or analysis.

V. Samples

In some embodiments, the methods, compositions, systems, and devices of the present invention make use of samples that include a nucleic acid template. Samples may be derived from any suitable source, and for purposes related to any field, including but not limited to diagnostics, research, forensics, epidemiology, pathology, archaeology, etc. A sample may be biological, environmental, forensic, veterinary, clinical, etc. in origin. Samples may include nucleic acid derived from any suitable source, including eukaryotes, prokaryotes (e.g. infectious bacteria), mammals, humans, non-human primates, canines, felines, bovines, equines, porcines, mice, viruses, etc. Samples may contain, e.g., whole organisms, organs, tissues, cells, organelles (e.g., chloroplasts, mitochondria), synthetic nucleic acid, cell lysate, etc. Nucleic acid present in a sample (e.g. target nucleic acid, template nucleic acid, non-target nucleic acid, contaminant nucleic acid may be of any type, e.g., genomic DNA, RNA, plasmids, bacteriophages, synthetic origin, natural origin, and/or artificial sequences (non-naturally occurring), synthetically-produced but naturally occurring sequences, etc. Biological specimens may, for example, include whole blood, lymphatic fluid, serum, plasma, buccal, sweat, tear, saliva, sputum, cerebrospinal (CSF) fluids, amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs, aspirates (bone marrow, fine needle) or washes (e.g., oral, nasopharangeal, bronchial, bronchialalveolar, optic, rectal, intestinal, vaginal, epidermal, etc.) and/or other fresh, frozen, cultured, preserved (PAXgene, RNAlater, RNasin, etc.) or archived (formalin fixed paraffin-embedded (FFPE), fixed cell/lymphocyte pellet, etc.) biological specimens.

In some embodiments, samples that find use with the present invention are mixed samples (e.g. containing mixed nucleic acid populations). In some embodiments, samples analyzed by methods herein contain, or may contain, a plurality of different nucleic acid sequences. In some embodiments, a sample (e.g. mixed sample) contains one or more nucleic acid molecules (e.g. $1 \ldots 10 \ldots 10^2 \ldots 10^3 \ldots 10^4 \ldots 10^5 \ldots 10^6 \ldots 10^7, 10^8 \ldots 10^9$, etc.) that contain a target sequence of interest in a particular application. In some embodiments, a sample (e.g. mixed sample) contains zero nucleic acid molecules that contain a target sequence of interest in a particular application. In some embodiments, a sample (e.g. mixed sample) contains nucleic acid molecules with a plurality of different sequences that all contain a target sequence of interest. In some embodiments, a sample (e.g. mixed sample) contains one or more nucleic acid molecules (e.g. $1 \ldots 10 \ldots 10^2 \ldots 10^3 \ldots 10^4 \ldots 10^5 \ldots 10^6 \ldots 10^7 \ldots 108 \ldots 10^9$, etc.) that do not contain a target sequence of interest in a particular application. In some embodiments, a sample (e.g. mixed sample) contains zero nucleic acid molecules that do not contain a target sequence of interest in a particular application. In some embodiments, a sample (e.g. mixed sample) contains nucleic acid molecules with a plurality of different sequences that do not contain a target sequence of interest. In some embodiments, a sample contains more nucleic acid molecules that do not contain a target sequence than nucleic acid molecules that do contain a target sequence (e.g. $1.01:1 \ldots 2:1 \ldots 5:1 \ldots 10:1 \ldots 20:1 \ldots 50:1 \ldots 10^2:1 \ldots 10^3:1 \ldots 10^4:1 \ldots 10^5:1 \ldots 10^6:1 \ldots 10^7:1$). In some embodiments, a sample contains more nucleic acid molecules that do contain a target sequence than nucleic acid molecules that do not contain a target sequence (e.g. $1.01:1 \ldots 2:1 \ldots 5:1 \ldots 10:1 \ldots 20:1 \ldots 50:1 \ldots 10^2:1 \ldots 10^3:1 \ldots 10^4:1 \ldots 10^5:1 \ldots 10^6:1 \ldots 10^7:1$). In some embodiments, a sample contains a single target sequence that may be present in one or more nucleic acid molecules in the sample. In some embodiments, a sample contains a two or more target sequences (e.g. $2, 3, 4, 5 \ldots 10 \ldots 20 \ldots 50 \ldots 100$, etc.) that may each be present in one or more nucleic acid molecules in the sample.

In some embodiments, a sample comprises a concentration of nucleic acid molecules that is sufficiently high to make partitioning the sample into partitions whereby some of the partitions contain zero nucleic acid molecule not feasible (e.g. sample would require too many partitions for analysis).

In some embodiments, various sample processing steps may be accomplished to prepare the nucleic acid molecules within a sample, including, but not limited to cell lysis, restriction digestion, purification, precipitation, resuspension (e.g. in amplification buffer), dialysis, etc. In some embodiments, sample processing is performed before or after any of the steps of the present invention including, but not limited to partitioning, amplification, re-amplification), amplicon detection, amplicon isolation, sequencing, etc.

EXPERIMENTAL

Example 1 dPCR Competitive

In some embodiments, the present invention provides methods quantitiation of one or more target nucleic acid sequences using cdPCR (SEE FIG. 1). Some embodiments of the present invention utilizing cdPCR are conducted using one or more of the following reagents, procedures, and analysis.

Sample nucleic acid is obtained from any suitable source, and is extracted and/or processed according to known methods to obtain nucleic acid suitable for amplification by PCR. A PCR reaction mixture is created using any customary or suitable concentrations of standard amplification reagent including: primer oligonucleotides specific for target nucleic acid and internal standard nucleic acid, fluorescent probes (i.e. differentially labeled probes specific for the target sequence and probe), DNA polymerase enzyme, amplification buffer, deoxynucleotides, internal standard (IS) nucleic acid, etc. The IS nucleic acid is added to the reaction mixture such that the concentration will produce a sufficient number of partitions containing 0 initial copies of the IS per partition (e.g. $\lambda_{IS} \approx 0.01\text{-}1$, where $\lambda_{IS}$ is the average number of IS copies per partition). [In general, when $\lambda_{IS}=1$, there are approximately and equal number of partitions containing zero initial IS copies and 1 initial IS copy.] The PCR reagents are added to the nucleic acid sample at concentrations known by those of skill in the art to be appropriate for PCR amplification (e.g. dPCR). The sample is then partitioned by any suitable methods (e.g. array micro-chambers, microplate wells, emulsion droplets, microfluidics, etc.) described herein to produce reaction subvolumes containing less than 1 (e.g. $\lambda_{IS} \approx 0.01\text{-}1$) molecules per partition. The partitions are subjected to thermal cycling conditions sufficient to amplify template nucleic acids in the reaction subvolumes. The fluorescence of each reaction subvolume is then measured for each fluorescent probe (e.g. target probe, IS probe).

The IS fluorescence and target fluorescence for each partition are correlated, and a determination is made as to whether the target nucleic acid meets the qualifications for direct analysis by dPCR methods (e.g. a number of partitions contain zero target molecules sufficient for quantitative assessment by Poisson analysis). If the target nucleic acid does not meet the criteria for Poisson analysis, partition responses are sorted into two groups according to the presence or absence of IS amplicons, i.e., detected fluorescence from the IS probe. Partitions exhibiting IS response in group 1 and partitions without IS response in group 2.

The average target response is calculated for the IS-containing partitions ($I_{group1}$) according to:

$$\langle I_{group1} \rangle = \frac{\sum_i^{group1} I_{target}(i)}{N_1} - \langle^{nonreactive}I_{target}\rangle$$

Wherein $^{group1}I_{target}(i)$ is the intensity measured for reaction subvolume i, and $N_1$ is the number of subvolumes exhibiting both target and IS fluorescence. $\langle^{nonreactive}I_{target}\rangle$ is the estimate for the fluorescence intensity in the target response detection channel when no target is present, namely the nonreactive background fluorescence level. i is summed over the $N_1$ partitions exhibiting both target and IS fluorescence.

The average target response is calculated for the no-IS partitions ($I_{group2}$) according to:

$$\langle I_{group2} \rangle = \frac{\sum_i^{group2} I_{target}(i)}{N_2} - \langle^{nonreactive}I_{target}\rangle$$

Wherein $^{group2}I_{target}(i)$ is the intensity measured for reaction subvolume i, and $N_2$ is the number of subvolumes exhibiting target but not IS fluorescence. i is summed over the $N_2$ partitions that do not exhibit IS fluorescence.

The percent change in target response with IS-competition is calculated according to:

$$\% \text{ change with competition} = \frac{\langle I_{group2}\rangle - \langle I_{group1}\rangle}{\langle I_{group2}\rangle} \times 100\%$$

The average number of target copies per reaction ($\lambda$) is calculated from the % change in target response with IS-competition according to:

$$\lambda = \frac{1}{\% \text{ change with competition}} \times \frac{N_1 + N_2}{N_1} \times \ln\left[\frac{N_1 + N_2}{N_2}\right]$$

The number of target copies measured for the total number of reaction subvolumes is calculated from $\lambda$ by multiplying the number of partitions, $N_1 + N_2$. The number of target copies in the total reaction is calculated according to:

$$\frac{\text{target copies}}{\text{total reaction}} = \lambda \times \frac{\text{total reaction volume}}{\text{average volume of partition}}$$

Example 2 dPCR Late

Figure 2:
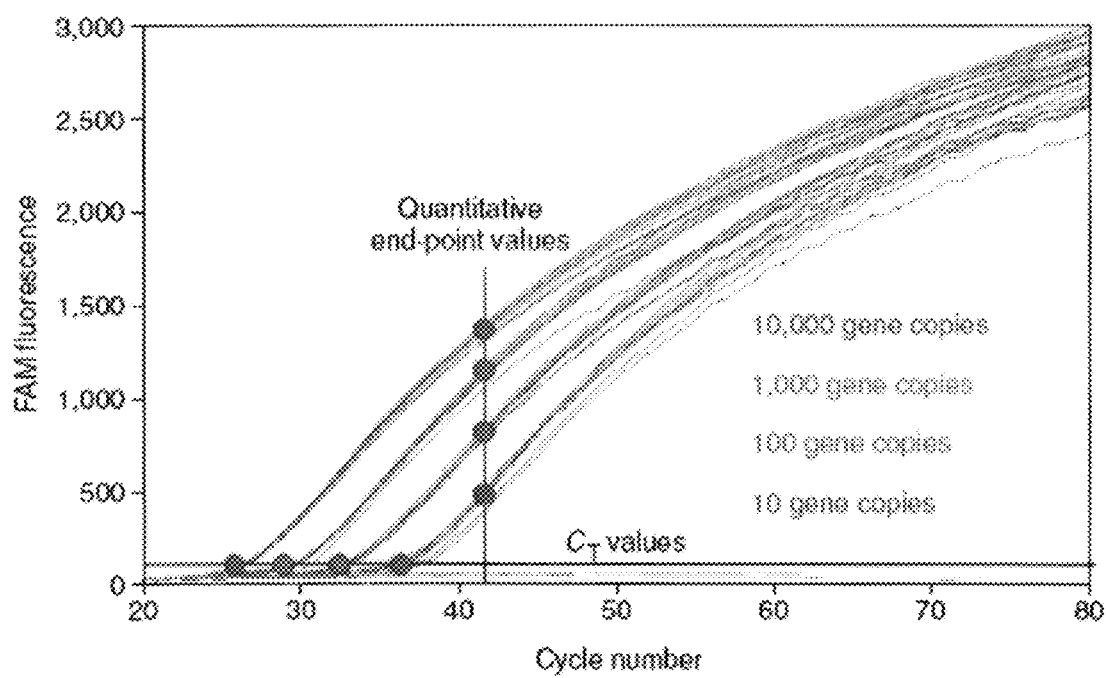
FIG. 2 shows a graph demonstrating the end-point relationship between fluorescence and initial gene-copy number using LATE-PCR.

Digital PCR using LATE-PCR assay design enhancements, takes advantage of the fact that fluorescence intensity detected after a fixed number of cycles of LATE-PCR, e.g. 40 cycles, correlates with initial template concentration (SEE FIG. 2). The final fluorescence level after amplification by LATE-PCR has a strong relationship to the log of the starting concentration. Furthermore, final fluorescence levels display reduced scatter at the LATE-PCR linear endpoint compared to exponential end-point values obtained by traditional real-time methods, enabling more precise target quantitation. Thus, combining LATE-PCR, which generates generally linear amplification responses in the later stages of cycling, provides a means to extend the dynamic range of dPCR. In order to retain the desired target specificity and avoid potential off-target mis-priming artifacts, it is preferred that the concentration-adjusted melting temperature of the Limiting Primer at the start of the amplification is 3-10° C. higher than the concentration-adjusted melting temperature of the Excess Primer at the start of the amplification. Quantitation using dPCR LATE may require running calibration samples at one or more known concentrations to create a calibration curve relating final fluorescence level to starting concentration.

Although the invention has been described in connection with specific preferred embodiments, it should be understood that the invention as claimed should not be unduly limited to such specific embodiments. Various modification and variation of the described methods and compositions of the invention will be apparent to those skilled in the art without departing from the scope and spirit of the invention. Indeed, various modifications of the described modes for carrying out the invention understood by those skilled in the relevant fields are intended to be within the scope of the following claims. All publications and patents mentioned in the present application and/or listed below are herein incorporated by reference.

We claim:

1. A method of quantitating target nucleic acid molecules in a sample comprising:
   a) separating said sample into a plurality of partitions, wherein said sample comprises: a mixture of nucleic acid molecules; amplification reagents; detection reagents; and internal standard nucleic acid molecules having identical primer binding sequences as said target nucleic acid molecules, wherein said internal standard nucleic acid molecules are added to said mixture at a concentration to produce a number of partitions containing zero or 1 copies of said internal standard molecules per partition; wherein said mixture of nucleic acid molecules is not diluted prior to addition of said amplification reagents, said detection reagents, and said internal standard nucleic acid molecules; wherein a portion of said plurality of partitions contains zero copies of said internal standard nucleic acid molecules; wherein a portion of said plurality of partitions contains zero copies of said target nucleic acid molecules; wherein said plurality of partitions comprises, on average, 2-100 nucleic acid molecules per partition and wherein said portion of said plurality of said partitions that contains zero or 1 copies of said internal standard nucleic acid molecules is sufficient in number to allow application of Poisson statistics;

b) treating said plurality of partitions under amplification conditions such that said target nucleic acid molecules are amplified to produce detectable target amplicons in one or more of said partitions, and said internal standard nucleic acid molecules are amplified to produce detectable internal standard amplicons in one or more of said partitions, wherein said detectable target amplicons and said detectable internal standard amplicons are differentially detectable;

c) determining a change in amplification of said target nucleic acid molecules in said plurality of partitions in response to primer competition from said internal standard nucleic acid molecules; and d) calculating an initial number of target nucleic acid molecules that are present in said sample before said sample has been separated into said plurality of partitions.

2. The method of claim 1, wherein said detection reagents comprise a first labeled probe configured to bind to said target sequence, and a second labeled probe configured to bind to said internal standard sequence, wherein said first labeled probe and said second labeled probe are differentially detectable.

3. The method of claim 2, wherein said first labeled probe and said second labeled probe comprise different fluorescent labels.

4. The method of claim 1, wherein said sample is selected from an environmental sample, a biological sample, a clinical sample, and a forensic sample.

5. A method of quantitating target nucleic acid molecules in a sample comprising:
   a) separating said sample into a plurality of partitions wherein said target nucleic acid molecules differ in number per a plurality of partitions; wherein said plurality of partitions comprise, on average, 100 or more nucleic acid molecules per partition; wherein said sample comprises: a mixture of nucleic acid molecules; internal standard nucleic acid molecules having identical primer binding sequences as said target nucleic acid molecules; amplification reagents for non-symmetric nucleic acid amplification; and detection reagents; wherein said mixture of nucleic acid molecules is not diluted prior to addition of said amplification reagents for non-symmetric nucleic acid amplification, said detection reagents, and said internal standard nucleic acid molecules; wherein a portion of said plurality of partitions contains zero copies of said target nucleic acid molecules;
   b) amplifying said target nucleic acid molecules by said non-symmetric nucleic acid amplification process to produce target amplicons;
   c) detecting said target amplicons in said plurality of partitions using said detection reagents; and
   d) correlating an intensity produced by said detection reagents following said non-symmetric nucleic acid amplification to an initial concentration of said target nucleic acid molecules in said sample.

6. The method of claim 5, wherein said amplification reagents comprise one excess primer and one limiting primer.

7. The method of claim 5, wherein said non-symmetric amplification process is a linear-after-the-exponential PCR (LATE-PCR) amplification process.

8. The method of claim 5, wherein said detection reagents comprise fluorescent labels.

9. The method of claim 8, wherein said detection reagents comprise fluorescently labeled probes.

10. The method of claim 5, wherein said detecting is an end-point detection following completion of said non-symmetric amplification process.

11. The method of claim 5, wherein said sample is selected from an environmental sample, a biological sample, a clinical sample, and a forensic sample.

* * * * *